(12) United States Patent
Eckhous et al.

(10) Patent No.: US 9,433,781 B2
(45) Date of Patent: Sep. 6, 2016

(54) METHOD AND APPARATUS FOR IMPROVING ELECTRODE-SKIN CONTACT

(75) Inventors: Shimon Eckhous, Haifa (IL); Lion Flyash, Nazareth (IL)

(73) Assignee: SYNERON MEDICAL LTD., Yoqneam Illit (IL)

( * ) Notice: Subject to any disclaimer, the term of this patent is extended or adjusted under 35 U.S.C. 154(b) by 551 days.

(21) Appl. No.: 13/991,100

(22) PCT Filed: Nov. 29, 2011

(86) PCT No.: PCT/IL2011/000905
§ 371 (c)(1),
(2), (4) Date: Jun. 26, 2013

(87) PCT Pub. No.: WO2012/073232
PCT Pub. Date: Jun. 7, 2012

(65) Prior Publication Data
US 2013/0274841 A1    Oct. 17, 2013

Related U.S. Application Data (60) Provisional application No. 61/419,265, filed on Dec. 3, 2010, provisional application No. 61/480,613, filed on Apr. 29, 2011.

(51) Int. Cl.
*A61N 1/06* (2006.01)
*A61B 18/14* (2006.01)
*A61B 18/00* (2006.01)

(52) U.S. Cl.
CPC .................. *A61N 1/06* (2013.01); *A61B 18/14* (2013.01); *A61B 2018/0016* (2013.01); *A61B 2018/0019* (2013.01); *A61B 2018/0047* (2013.01); *A61B 2018/00107* (2013.01); *A61B 2018/00791* (2013.01); *A61B 2018/00875* (2013.01); *A61B 2018/1467* (2013.01)

(58) Field of Classification Search
CPC ....................................................... A61N 1/06
See application file for complete search history.

(56) References Cited

U.S. PATENT DOCUMENTS

| | | | |
|---|---|---|---|
| 4,736,752 A * | 4/1988 | Munck | A61N 1/0452 607/149 |
| 5,330,525 A | 7/1994 | Proctor | |
| 5,601,618 A * | 2/1997 | James | A61F 7/007 607/148 |
| 6,526,303 B1 | 2/2003 | Scampini | |
| 2002/0107543 A1* | 8/2002 | Voznesensky | A61F 7/007 607/3 |
| 2003/0088167 A1* | 5/2003 | Fendrock | A61B 5/0408 600/372 |
| 2003/0097165 A1* | 5/2003 | Krulevitch | A61N 1/0543 760/115 |

(Continued)

*Primary Examiner* — Kaitlyn Smith
(74) *Attorney, Agent, or Firm* — Vorys, Sater, Seymour and Pease LLP; William L. Klima (57) ABSTRACT

Disclosed are a method and apparatus for improving electrode-skin contact. The electrode is a segmented electrode having an array of energy applying surfaces mounted on a substrate via at least one electro-mechanical energy converting element to a segment of skin. The electrode is coupled to the skin and a mechanism monitors the quality of electrode-skin contact under the energy applying surfaces. Activation of the electro-mechanical energy converting elements effects mechanical movement of the skin and energy applying surfaces and redistributes the skin surface coupled to the electrodes conforming it to the topography of the RF energy applying surfaces to optimize electrode-skin contact. The segmented electrode is operative to be disposable while enabling reuse of costly components of the electrode.

21 Claims, 11 Drawing Sheets

(56) References Cited

U.S. PATENT DOCUMENTS

| | | |
|---|---|---|
| 2004/0210214 A1 | 10/2004 | Knowlton |
| 2005/0136639 A1* | 6/2005 | Davidson .......... H01L 21/76838 |
| | | 438/612 |
| 2005/0197671 A1 | 9/2005 | Vlad |
| 2008/0147146 A1* | 6/2008 | Wahlgren ........... A61B 5/04001 |
| | | 607/61 |
| 2009/0177131 A1 | 7/2009 | Dar et al. |
| 2010/0298895 A1 | 11/2010 | Ghaffari et al. |
| 2010/0312307 A1* | 12/2010 | Minogue .............. A61N 1/0452 |
| | | 607/48 |

\* cited by examiner

METHOD AND APPARATUS FOR IMPROVING ELECTRODE-SKIN CONTACT

TECHNICAL FIELD

The device and method relate to the field of body shaping RF devices and more specifically to the use of RF electrodes in cosmetic body shaping devices.

BACKGROUND

The practice of using heat energy for cosmetic body shaping is known. Heating the skin and underlying tissues causes tissue shrinkage and produces the desired cosmetic effect.

The use of RF energy emitting devices for cosmetic body shaping is also known. Cosmetic body shaping treatment is administered using an applicator including one or more RF electrodes. The electrodes' RF energy applying surface, coupled with the surface of the skin, generate in the skin an electric current that in-turn generates heat in the skin and underlying subcutaneous tissues to create the desired effect of tissue shrinkage.

Frequently the coupling of such an electrode to the skin results in partial contact only between the energy applying surface of the electrode and the skin in contact with the electrode surface. Partial contact between the RF electrode and the skin results in reduced efficiency of the application of RF energy from the electrode energy applying surface to the skin coupled to the surface and non-uniform distribution of heat produced in the tissue underlying the surface of the electrode, overheating one area and under-heating another, bringing about undesirable, less than optimal results of the cosmetic treatment as a whole.

To improve contact, a medium such as electrically-conductive and/or adhesive gel is applied to the skin prior to coupling of the RF electrode.

Recently, the at-home use of personal cosmetic body-shaping devices have become popular. Disposable components, primarily components that come in contact with the body, are employed to replace reusable components wherever possible to make such devices user-friendly and less costly as well as more hygienic. Since some device components may be quite expensive and/or non-disposable, creative solutions are sometimes necessary to enable reuse of such components while maintaining disposability of others.

The present device and method provide a solution for improving the contact and adhesion of a disposable RF electrode to the underlying surface of the skin increasing the efficiency of RF energy applying to the skin and providing a more uniform heat distribution in the skin bringing about safer and more satisfactory cosmetic treatment results.

SUMMARY

In accordance with one exemplary embodiment of the current method and apparatus a segmented electrode is provided including an array of RF energy applying surfaces, mounted on a substrate via electrical-mechanical energy converting elements and coupled to the surface of skin.

In accordance with another embodiment the segmented electrode may also include one or more electrode-to-skin contact sensing mechanisms, such as, for example, a skin impedance sensing or monitoring mechanism, operative to monitor the quality of the coupling contact between all of, or each specific, RF energy applying surfaces to the skin.

Electrical activation of electro-mechanical energy converting elements may bring about expansion and contraction of the elements resulting in mechanical movement such as vibration. Such a mechanical movement may cause the surface of a segment of skin to glide under the electrode, distribute more uniformly and conform to the topography of the RF energy applying surfaces bringing about an improved and optimized electrode-skin contact.

In accordance with still another embodiment of the current method and apparatus the substrate may also be made of electro-mechanical energy converting elements made of a material similar to or different than that of the energy converting elements.

In accordance with another embodiment of the current method and apparatus the segmented electrode may also include an adhesive gel dispenser.

In accordance with another embodiment of the current method and apparatus the segmented electrode may be disposable en bloc.

In accordance with another embodiment of the current method and apparatus the segmented electrode may be partially disposable, having one or more reusable portions.

In accordance with another embodiment of the current method and apparatus the segmented electrode is operative to be disposable while enabling reuse of costly components of the electrode.

BRIEF DESCRIPTION OF THE DRAWINGS

The method and the apparatus are particularly pointed out and distinctly claimed in the concluding portion of the specification. The method and the apparatus, however, both as to organization and method of operation, may best be understood by reference to the following detailed description when read in conjunction with the accompanying drawings, in which like reference characters refer to the same parts throughout the different views. The drawings are not necessarily to scale, emphasis instead being placed upon illustrating the principles of the method and apparatus. In the drawings:

DETAILED DESCRIPTION

The terms "electro-mechanical energy converting element" and "mechanical vibrating elements" are used interchangeably in the present disclosure and mean elements operative to convert voltage received from a source of electric energy to mechanical energy such as, for example, mechanical vibration.

As used herein, the term "good quality of the electrode-to-skin contact" relates to firm or almost complete contact between the electrode surface and the skin. Contact that does not include voids, air traps, and similar. Good contact quality is defined by almost complete or complete contact between the electrode surface and the skin. Good contact facilitates electrical and thermal coupling between the electrode surface and the skin. In a similar mode the term "quality of the electrode-to-skin contact" could be related to ultrasound transducers surface-to-skin contact.

Figure 1A:
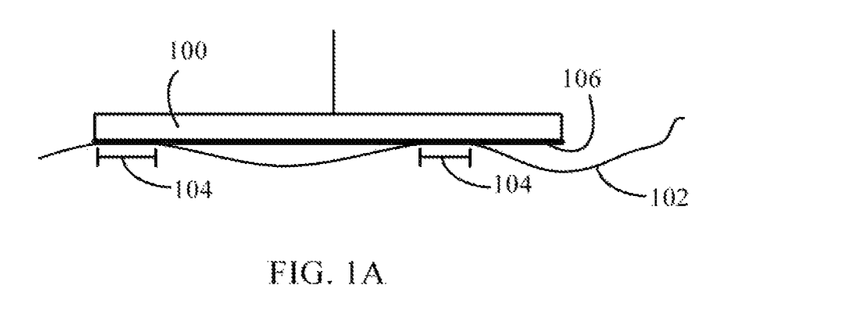
FIGS. 1A, 1B and 1C are simplified cross-sectional illustrations of a commonly employed non-segmented RF electrode.
Figure 1B:
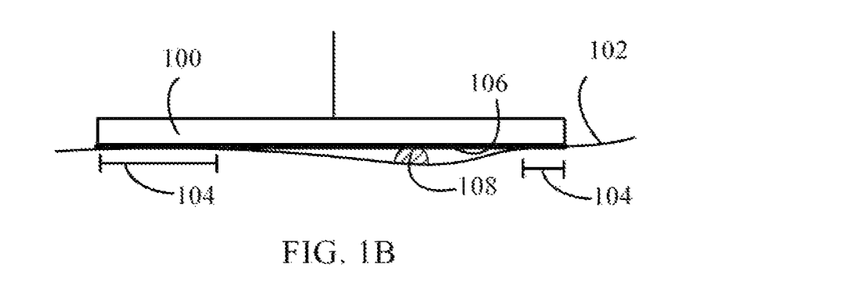
Figure 1C:
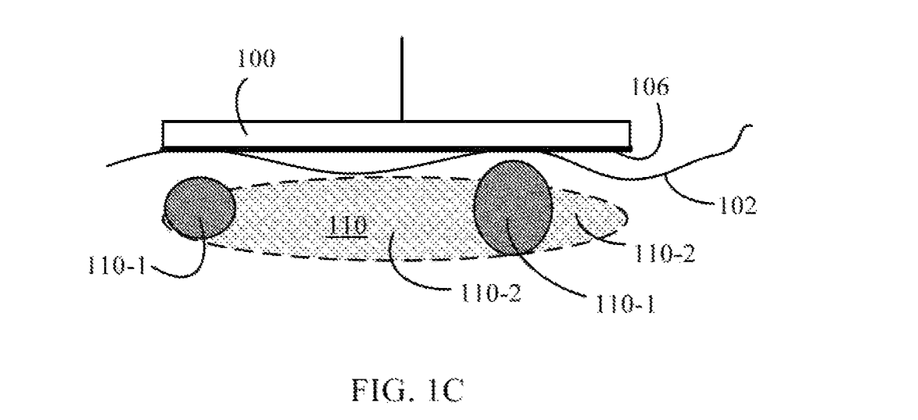

Referring now to FIGS. 1A, 1B and 1C, which are simplified cross-sectional illustrations of a commonly employed non-segmented non-vibrating RF electrode. In FIG. 1A, a commonly used RF electrode 100 is coupled to an irregular surface of a segment of skin 102. As shown in FIG. 1A, only areas 104 of an energy applying surface 106 of RF electrode 100 are in contact with the irregular surface of segment of skin 102.

As shown in FIG. 1B, a blemish 108, which may cause or be an air pocket, distances a segment of the surface of skin 102 under and adjacent to blemish 108 preventing acceptable electrode-skin contact under the RF electrode 100 except for at the limited areas 104 under energy applying surface 106 of RF electrode 100.

Both situations shown in FIGS. 1A and 1B depict partial contact between energy applying surface 106 of RF electrode 100 and the surface of skin 102 resulting in reduced efficiency of the application of RF energy from the electrode energy applying surface 106 coupled to the surface of skin 102. This, as shown in FIG. 1C, may result in a non-uniform distribution of heat produced in a tissue segment 110 underlying surface 106 of the electrode, for example, overheating one area 110-1 and under-heating a different area 110-2, bringing about non-uniform heating of tissue segment 110, which is a less than optimal and an undesirable result of the cosmetic treatment as a whole.

Figure 2A:
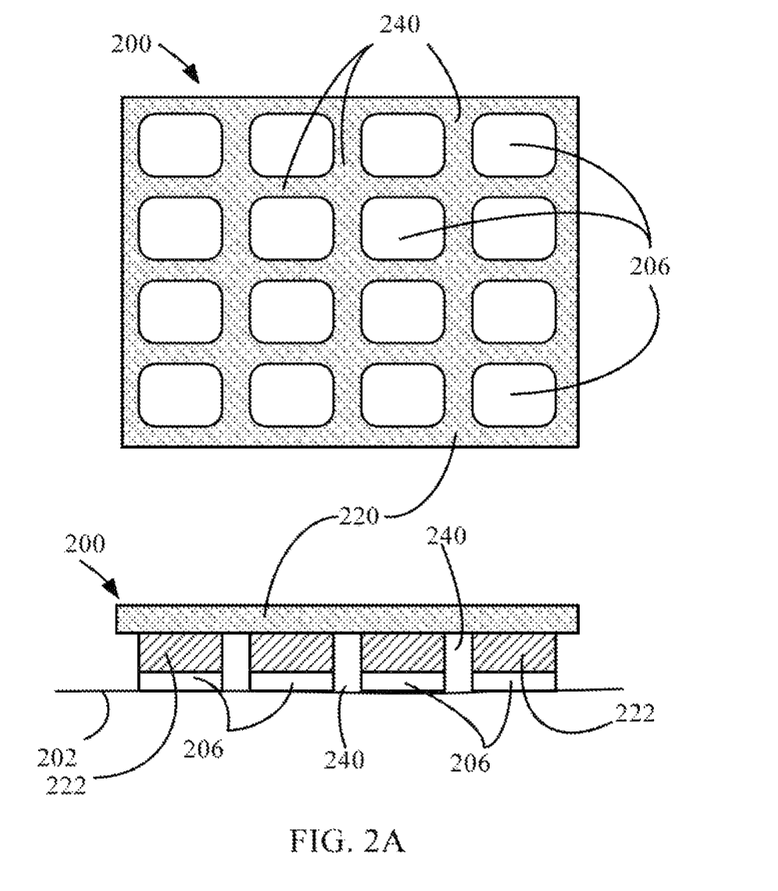
FIGS. 2A and 2B are simplified plan view and cross-sectional view illustrations of two exemplary embodiments of an RF electrode with improved electrode-skin contact and adhesion in accordance with the current method and apparatus.
Figure 2B:
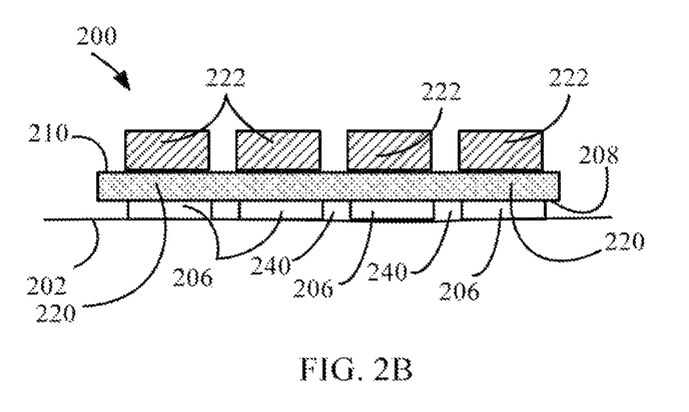

Reference is now made to FIGS. 2A and 2B, which are simplified plan view and cross-sectional view illustrations of an exemplary embodiment of an RF electrode with improved electrode-skin contact and adhesion in accordance with the current method and apparatus and as described in assignee's U.S. Provisional Patent Application No. 61/419,465. As shown in FIG. 2A, a segmented electrode 200 includes an array of RF energy applying surfaces 206 defining recesses 240 therebetween, mounted on a substrate 220 and coupled to the surface of skin 202. Substrate 220 may be made of one or more materials selected from a group consisting of rigid, semi-rigid, resilient, stretchable and contractible materials such as rubber, elastic band, flexible and stretchable mesh or similar. Such materials may include, but not be limited to, thin and/or flexible polymers such as polyethylene (PE), polypropylene (PP) or polyvinyl chloride (PVC). The thickness of substrate 220 may be in the range between 0.1 mm and 1.5 mm.

Electro-mechanical energy converting elements 222 may be disposed between and in contact with RF energy applying surfaces 206 and substrate 220. Additionally or alternatively, and as shown in FIG. 2B, RF energy applying surfaces 206 may be directly attached to substrate 220 on a first surface 208 of substrate 220 and electro-mechanical energy converting elements 222 may be directly attached to substrate 220 on a second surface 210 of substrate 220, opposite to first surface 208. Elements 222 may be made of one or more electro-mechanical converting material such as piezoelectric materials, electro-strictive materials, electronic and/or ionic electro-active polymers (EAP) such as Polyvinylidene Fluoride (PVDF) and other similar materials.

RF energy applying surfaces 206 of the array may be coated with an electrically conductive semi-adhesive, adhesive or granular coating to improve adhesion of RF energy applying surfaces 206 to the skin but still allowing gliding movement and redistribution of surface of skin 202 under RF energy applying surfaces 206.

Each of the electrodes 206 of segmented electrode 200 is individually addressable and enables skin impedance monitoring by a controller 330 (FIG. 3) between each pair of operating electrodes in course of electrode operation. Impedance monitoring, as disclosed in Patent Cooperation Treaty Application PCT/IL2009/000856 to the same Assignee may be operative to monitor the quality of the coupling contact between RF energy applying surfaces 206 and surface of skin 202, and provide feedback to a controller 330 (FIG. 3) regarding the quality of electrode-skin contact as well as skin temperature. Since each of the energy applying surfaces 206 is individually addressable and distributed throughout electrode 200 the impedance monitoring by controller 330 may be indicative of the location of areas under RF energy applying surfaces 206 at which electrode 200-skin 202 contact is poor.

As described in Assignee's U.S. Provisional Patent Application No. 61/419,465, electrical activation of electro-mechanical energy converting elements 222 by controller 330 (FIG. 3) may bring about expansion and contraction of elements 222 resulting in a rapid energy converting elements 222 mechanical movement such as vibration. Such a mechanical movement may apply variable pressure to the skin surface and urge the surface of a segment of skin 202 to glide under RF energy applying surfaces 206 and distribute more uniformly and conform to the topography of RF energy applying surfaces 306, or, alternatively, to glide resilient RF energy applying surfaces 306 over and conform to the topography of the surface of a segment of skin 202, bringing about an improved and optimized electrode 200-to-skin 202 contact. A positive feedback mechanism may bring controller 330 to cease all or part of the mechanical movement.

Figure 3:
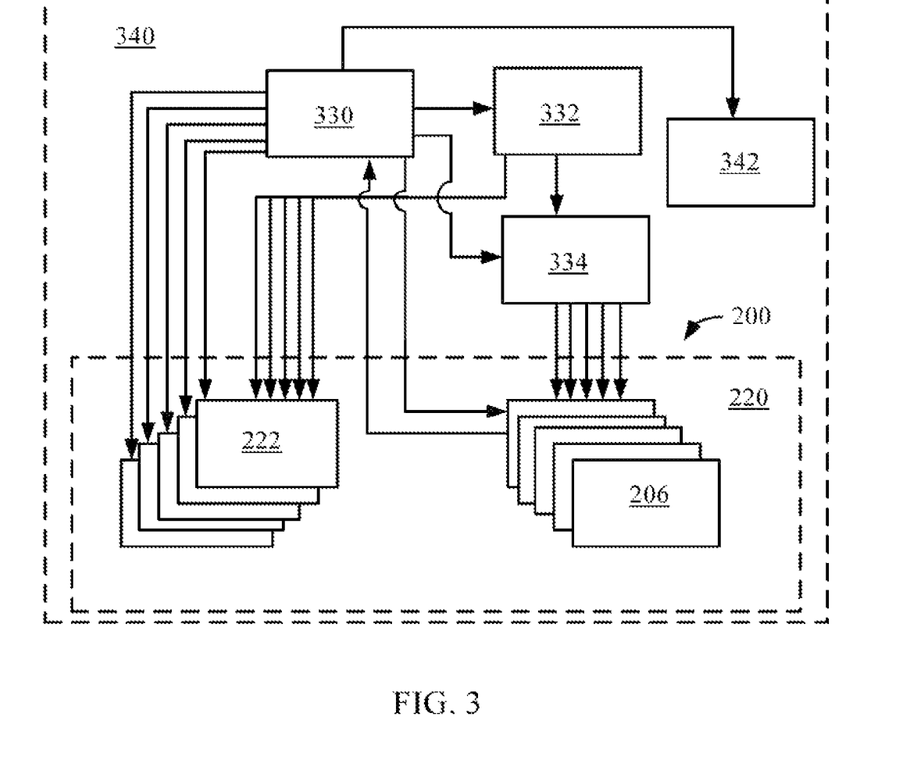
FIG. 3 is a simplified block diagram of the electrical and feedback communication between components of the apparatus for improving electrode-skin contact and adhesion in accordance with still another exemplary embodiment of the current method and apparatus.

Referring to FIG. 3, which is a simplified block diagram of the electrical and feedback communication between components of the apparatus for improving electrode-skin contact and adhesion in accordance with the current method and apparatus. Such components may include a housing 340 including one or more controllers 330, sources of energy 332, RF energy generators 334 supplying RF energy to one or more individual RF energy applying surfaces 206 or electrodes mounted on substrate 220 via one or more electro-mechanical energy converting elements 322.

Controller 330 initially provides a test RF voltage sufficient to monitor skin impedance of each pair of operating electrodes indicating state of the quality of electrode 200-to-skin 202 contact. Controller 330, in accordance with the measured skin impedance and a predetermined protocol, activates electro-mechanical energy converting elements 222 to bring the surface of skin 202 (FIG. 2) to glide under RF energy applying surfaces 206 and redistribute more uniformly and conforming to the topography of RF energy applying surfaces 206, bringing about an improved and optimized electrode 200-to-skin 202 contact. When such an improved contact takes place the change in skin impedance is detected by controller 330, which in turn activates source of energy 332 and RF energy generator 334 applying RF energy to the surface of skin 202 (FIG. 2) via RF energy applying surfaces 206 of electrode 200.

Electro-mechanical energy converting elements 222 may be activated separately, consecutively or concomitantly by controller 330 to provide partial and/or directional vibration to each individual energy applying surfaces 206 in accordance with the skin impedance values and a predetermined treatment protocol.

Controller 330, may be operative to analyze measured impedance values and activate only selected electro-mechanical energy converting elements 222 to achieve redistribution of surface of skin 202 only in areas under RF energy applying surfaces 206 where the skin impedance value indicate poor electrode 200-to-skin 202 contact.

Additionally, substrate 220 may also include or be coupled to one or more mechanical vibrating elements 342, which, for example, may include but not be limited to a piezoelectric transducer, a pair of electromagnetic elements or a small mechanism having an eccentric weight fixed to a shaft, which may be mounted on or be coupled to a motor and be controlled by controller 330, as will be described below in detail.

Figure 4A:
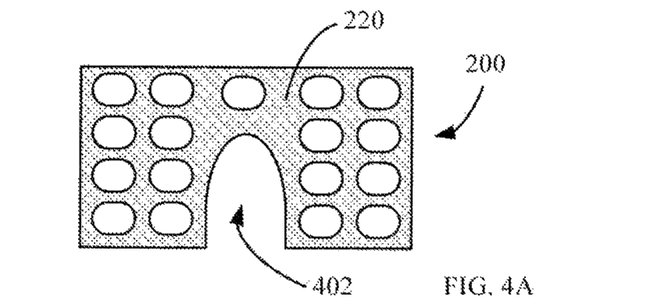
FIGS. 4A, 4B and 4C are simplified plan view illustrations of other exemplary embodiments of an RF electrode with improved electrode-skin contact and adhesion in accordance with the current method and apparatus.
Figure 4B:
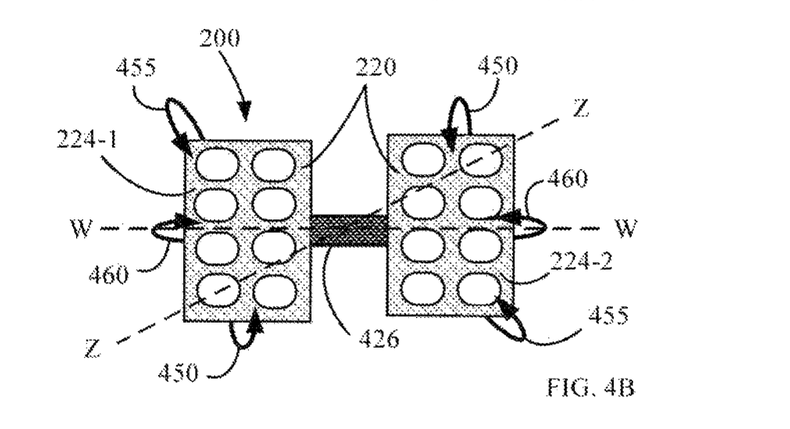
Figure 4C:
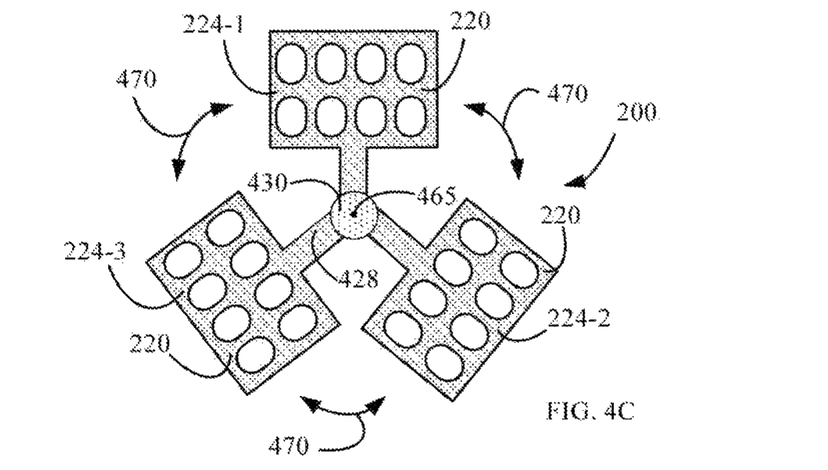

Reference is now made to FIGS. 4A, 4B and 4C, which are other embodiments of electrode 200 of FIGS. 2A, 2B and 2C in accordance with the current method and apparatus. Substrate 220 may be shaped in a form allowing conforming substrate 220 to the topography of the skin of the body part to which RF electrode 200 is to be coupled. For example, in FIG. 4A substrate 220 includes a cut-out 402 to accommodate a protruding body part such as a nose. This allows better adhering of electrode 200 around such a protruding body part without distorting or warping substrate 220.

FIG. 4B illustrates another embodiment of the current method and apparatus in which substrate 220 of electrode 200 includes two or more portions 224-1 and 224-2 connected to each other via a bridge 426. Bridge 426 may be made of the same material as substrate 220 or a different material such as, but not limited to, an elastic expandable band, synthetic fabric, electrically conductive textile, or similar. Bridge 426 may be made of a resilient, semi-rigid or rigid material that enables the rotation of substrate 220 portions 224-1 and 224-2 at least about the longitudinal axis of bridge 426, for example, axis W-W as indicated by arrows 450 or axis Z-Z as indicated by arrows 455. Additionally or alternatively, bridge 426 may be folded or flexed in any other direction to enable electrode 200 to conform to the topography of the surface of the skin of a specific body part to be cosmetically treated as shown, for example, by arrows 460.

In another embodiment in accordance with the current method and apparatus, substrate 220 portions 224-1 and 224-2 may include one or more energy applying surfaces 106 and be disposable in which case bridge 426 may serve as a reusable docking platform for electrode 100 substrate 220 portions 224-1 and 224-2 as well as reusable electrode 100 components such as controller 330 (FIG. 3), an adhesive gel dispenser (FIGS. 5B, 6A and 6B), a motor (FIGS. 5A, 7A, 7B and 7C), a printed circuit board (PCB) (FIGS. 5A and 5B) and other reusable components as will be explained in greater detail below.

Alternatively, substrate 220 portions 224-1 and 224-2 may be reusable and accommodate disposable energy applying surface 106 (described in assignee's U.S. Provisional Patent Applications Nos. 61/393,902 and 61/427,305) in which case reusable bridge 426 together with substrate 220 portions 224-1 and 224-2 may serve as a docking platform for electrode 100 (FIG. 1) reusable components as described hereinabove.

FIG. 4C illustrates another embodiment of the current method and apparatus in which three or more substrate 220 portions 224-1, 224-2 and 224-3 are connected to each other via a bridge 428 having a plurality of arms. Bridge 428 may be made of a material similar to that of bridge 426 described above, a semi-rigid material or a rigid material.

Bridge 428 may also enable the rotation, folding and flexing of substrate 220 portions 224-1, 224-2 and 224-3 as described in FIG. 4B above.

Additionally or alternatively, the plurality of arms of bridge 428 may also be connected to an articulated hub 430 so that to allow back-and-forth radial movement of portions 224-1, 224-2 and 224-3 about a center 465 of hub 430 as indicated by arrows 470 for better and/or more convenient positioning of electrode 200.

Additionally, similar to the embodiment described in FIG. 4B above, bridge 428 may also serve as a reusable docking platform for electrode 200 substrate 220 portions 224-1, 224-2 and 224-3 to accommodate disposable energy applying surface 106 as well as reusable components of electrode 200 such as controller 330 (FIG. 3), an adhesive gel dispenser (FIGS. 5B, 6A and 6B), a motor (FIGS. 5A, 7A, 7B and 7C), a printed circuit board (PCB) (FIGS. 5A and 5B) and other reusable components as will be explained in greater detail below.

It will be appreciated by persons skilled in the art that several electrodes, physically and electrically separate from each other, separately and individually controlled by controller 330 may also be placed on the body of a subject at various locations at any one time.

Figure 5A:
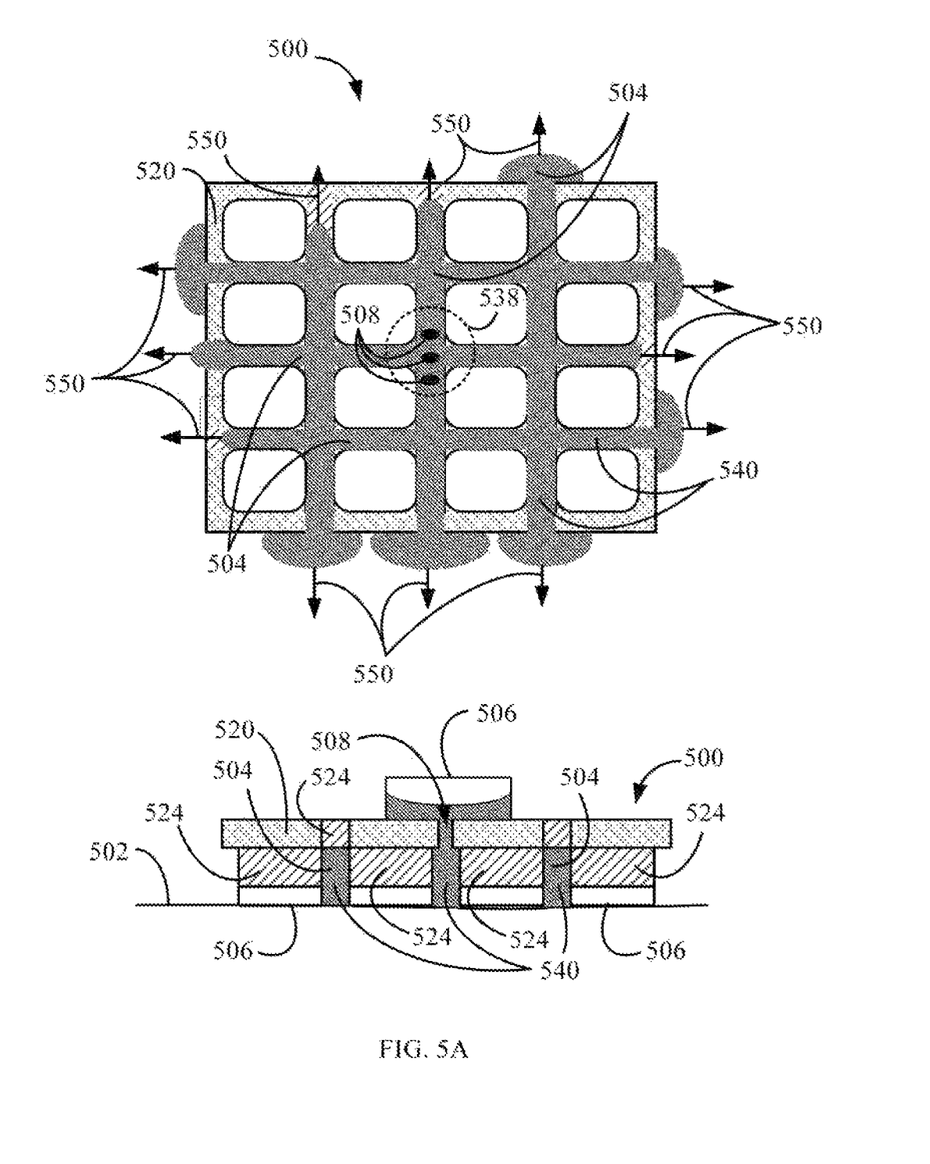
FIGS. 5A, 5B and 5C are simplified plan view and cross-sectional view illustrations of yet other exemplary embodiments of an RF electrode with improved electrode-skin contact and adhesion and gel dispenser in accordance with the current method and apparatus.

Reference is now made to FIG. 5A, which is a plan view and cross-sectional view simplified illustration of yet another exemplary embodiment of an RF electrode with improved and optimized electrode-skin contact and adhesion as described in Assignee's U.S. Provisional Patent Application No. 61/419,465. An adhesive electrically conductive substance such as adhesive electrically conductive gel 504 may be applied to the surface of skin 502 under electrode 500.

The application of adhesive coupling gel 504 may be performed manually or may be applied from a gel dispenser 506 included in or attached to electrode 500 through pores 508 in substrate 520 of electrode 500. A generous volume of adhesive coupling gel 504 may be applied to an area of skin smaller than the surface area of electrode 500. Activation of electro-mechanical energy converting elements 524 brings about not only redistribution of the surface of skin 502 under electrode 500 but also the urging of the applied adhesive coupling gel 504 along recesses 540 in the directions indicated by arrows 550, forcing out any air trapped in between electrode 500 and surface of skin 502 and filling any remaining gaps, further improving electrode-skin contact and adhesion.

It will be appreciated by persons skilled in the art that even though application of an adhesive coupling gel 504, which may be an electrically conductive coupling gel, improves to some extent RF electrode 500 contact with the surface of skin 4502, heat transfer and RF energy adhesive coupling gel 504 may not completely resolve or compensate for insufficient or poor electrode 500-skin 502 contact.

Electrically conductive coupling gel dispenser 506 may be a miniature gel pump and may be attached to a surface of electrode 500 substrate 520. Such a pump may be similar to the known in the art insulin patch pump such as the SteadyMed® Patch Pump from SteadyMed Ltd. (http://www.steadymed.com/contact.asp) or a bubble expansion activated gel dispenser 506 such as that described in U.S. Provisional patent application Ser. No. 12/684,381 to the same Assignee and illustrated in FIGS. 5B and 5C.

Figure 5B:
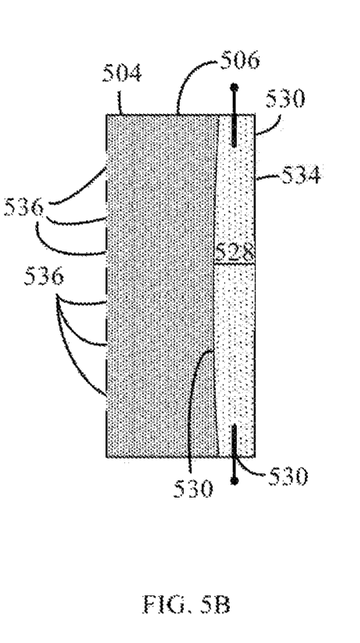
Figure 5C:
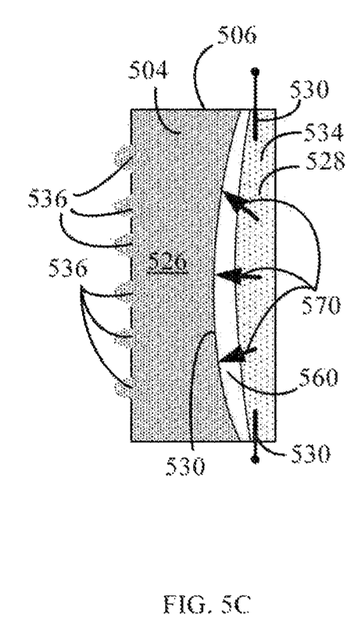

As shown in FIG. 5B dispenser 506 may include a first larger gel chamber 526 containing adhesive coupling gel 504 and a second smaller fluid chamber 528 with a resilient divider 530 therebetween. Fluid chamber 528 further comprises electrodes 530, supplied by power source 332 in housing 340 or attached to substrate 520 and an electrolyte-containing fluid 534.

When electrodes 530 are activated by controller 330 electrolysis occurs in fluid 534 creating a gas bubble 560 that expands in a direction indicated by the arrows 570 against resilient divider 530 which, in turn, urges adhesive coupling gel 504 out through one or more pores 536. Controller 330 may activate gel dispenser 506 only after impedance monitoring by controller 330 has indicated optimized electrode 500-to-skin 502 contact. Controller 330 may at this point in time activate RF energy applying surfaces 506 to deliver RF energy to skin 502.

It may be appreciated by those skilled in the art that adhesive coupling gel 504 need not necessarily be electrically conductive and may serve solely as a biocompatible adhering agent. In another embodiment in accordance with the current method and apparatus adhesive coupling gel 504 may serve as an adherent coupling gel that may include, but not be limited to, electrically conductive hydrogel materials such as Polyelectrolytes [polyvinylpyrrolidone (PVP) or Carboxymethyl cellulose), poly (2-acrylamido-2-methyl-1-propanesulfonic acid (PolyAMPS), polyethylene oxide (PEO)] and other conductive hydrogels.

Alternatively, on instances in which the application of an electrically conductive adhesive coupling gel is not desired for RF energy delivery, dispenser 506 may distribute the adhesive coupling gel at a central area 538 of substrate 520 or, for example, under reusable bridge 426 (FIG. 4B) or hub 430 (FIG. 4C). This enables adhering electrode 500 to skin 502 with minimal interference with the RF energy application by electrode energy applying surface 506 to skin 502 but still allowing gliding movement and redistribution of surface of skin 502 under RF energy applying surfaces 506.

Figure 7A:
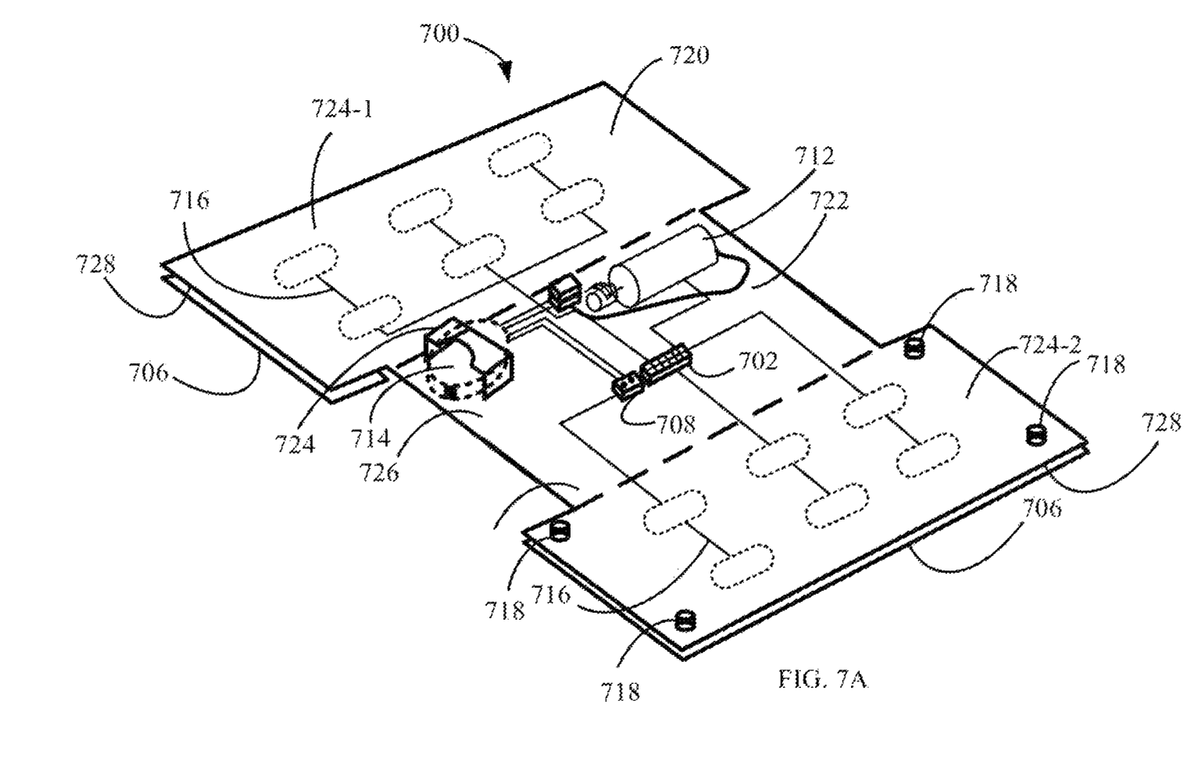
FIGS. 7A, 7B and 7C, which are elevated oblique and semi-exploded view, simplified illustrations of other exemplary embodiment in accordance with the current method and apparatus.
Figure 7B:
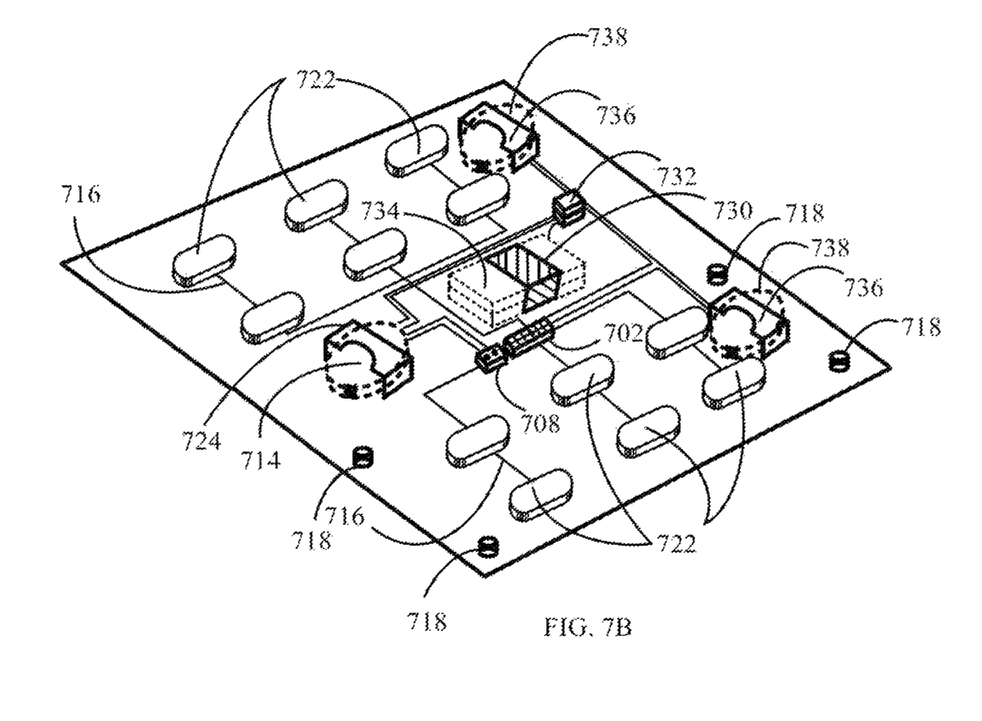
Figure 7C:
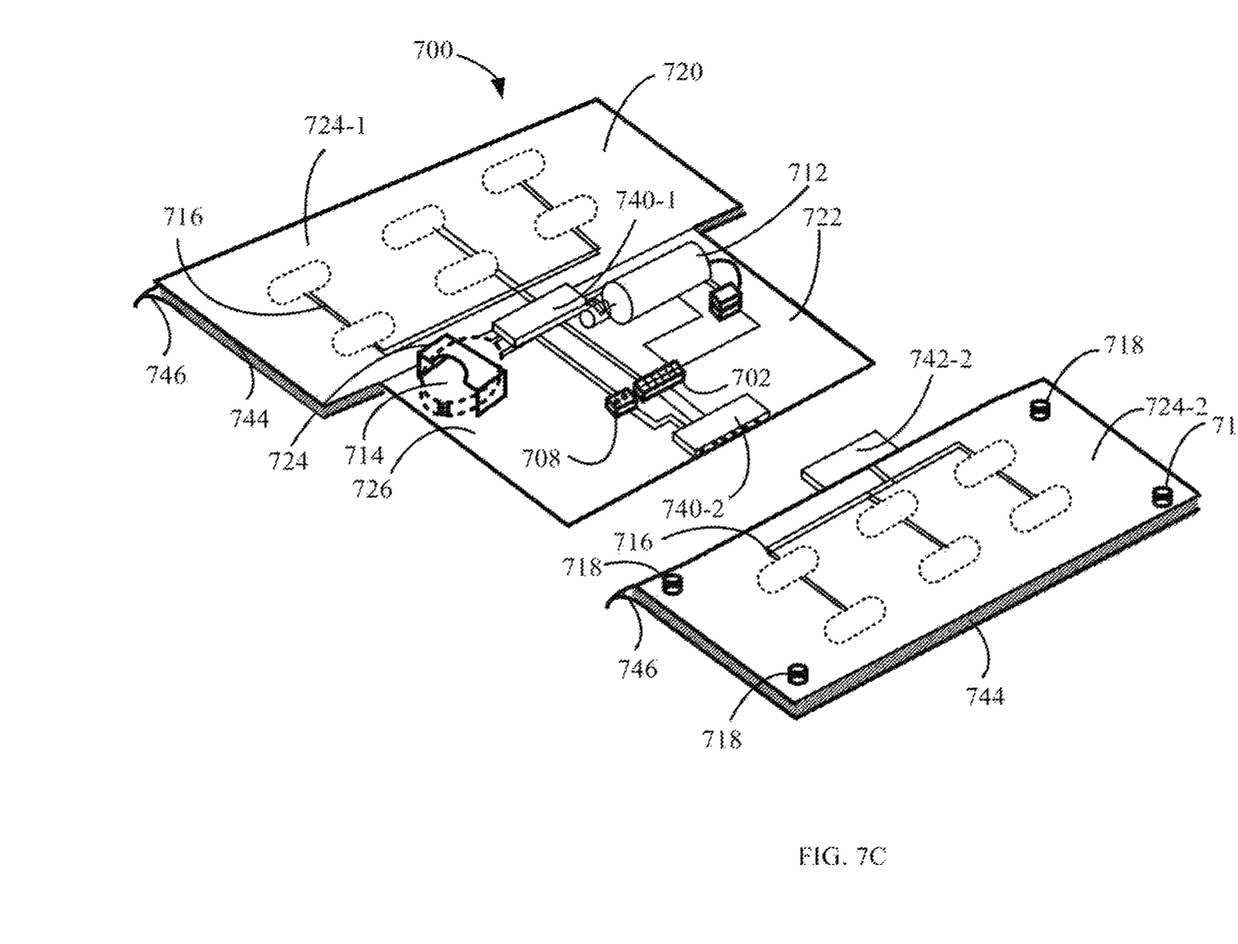

In still another embodiment, in accordance with the current method and apparatus, and as shown in FIG. 7C, disposable substrate 220 portions such as portions 224-1, 224-2 and 224-3 (FIGS. 4B and 4C) and portions 724-1 and 724-2 (FIGS. 7A, 7B and 7C) may be pre-coated with a coat 744 (FIG. 7C) of an adhesive gel protected by a protective thin-sheet peel-off layer 746.

Figure 6A:
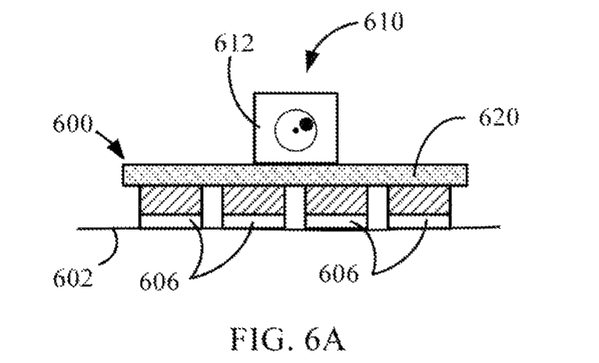
FIGS. 6A, 6B and 6C are simplified cross-sectional view illustrations of still other exemplary embodiments of an RF electrode with improved electrode-skin contact and adhesion in accordance with the current method and apparatus.
Figure 6B:
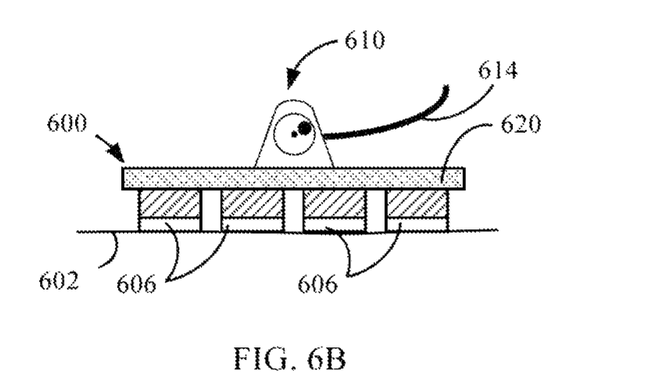
Figure 6C:
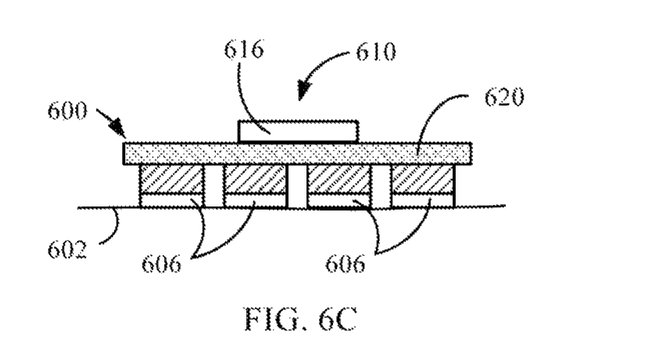

Reference is now made to FIGS. 6A, 6B and 6C, which are cross-section view simplified exemplary illustrations of another embodiment described in Assignee's U.S. Provisional Patent Application No. 61/419,465. One or more mechanical vibrating elements 342/610 may include, as shown in FIG. 6A, a vibration motor 612 of suitable size or, as illustrated in FIG. 6B, be driven via a flexible rotatable shaft 614 by an external motor (not shown).

Mechanical vibrating elements 610 in this embodiment may be mounted directly on substrate 620 of electrode 600. Such mechanical elements may be, for example, a known in the art flat (coin-type) vibration motor 616 as shown in FIG. 6C, such as Sanko Vibramotor® type 1E120 from Jameco Electronics, Belmont, Calif., a coin type vibration motor from Kata Company (http://www.motor-asia.com/index.html) or a micro cylinder (bar) type vibration motor such as a 4 mm Vibration Motor from Precision Microdrives Limited, London (https://secure.precisionmicrodrives.com).

The vibrating elements may be mounted to cause vibrations of substrate 620 in direction perpendicular or parallel to skin 602. Substrate 620 may be rigid, semi-rigid or resilient in nature, but sufficiently rigid to carry mechanical vibrating elements 610. Mechanical vibrating elements 610 amplitude and/or frequency may also be controlled by controller 330. Alternatively and optionally, vibrating elements 610 may further comprise a controller capable of adjusting the amplitude and/or frequency of the vibrations, independently or in coordination with controller 330 (FIG. 3).

A mechanical vibrating movement, produced by mechanical vibrating elements 610 may cause the surface of a segment of skin 602 to glide under electrode 600, distribute more uniformly and conform to the topography of the RF energy applying surfaces 606 bringing about an improved and optimized electrode-skin contact.

Reference is now made to FIGS. 7A, 7B and 7C, which are elevated oblique simplified illustrations of yet another embodiment in accordance with the current method and apparatus. FIG. 7A illustrates a reusable substrate 720 in which reusable bridge 726 connects between two portions 724-1 and 724-2 of substrate 720 and may function as a docking platform onto which portions 724-1 and 724-2 may be attached and detached from along broken lines 750 and disposed of following use. Alternatively, portions 724-1 and 724-2 of substrate 720 and may be integrally attached to reusable bridge 726. Energy applying surfaces 706 may be attached to surfaces 728 of portions 724-1 and 724-2 and detached from and disposed of following use.

Reusable substrate 720 may be of any geometric shape similar, for example purposes only, to the shapes portrayed in the description above in FIG. 4A, 4B or 4C, which may improve electrode-to-skin contact, measured by impedance monitoring of controller 330 as described above.

Reusable substrate 720 may be made of a rigid or semi-rigid material or any material that may be suitable for carrying the aforementioned reusable components of electrode 700.

Substrate 720 may carry or include a physical connector for reusable components of electrode 700 such as a connector 702 to controller 330, a vibration motor 712 and a printed circuit board (PCB) 716.

Substrate 720 may also include a rechargeable source of power such as battery 714 and/or a connector 708 to an external power source.

Alternatively, and as shown in FIG. 7B, electrode 700 may be disposable en bloc in which case substrate 720 may serve as a docking platform and include connectors and brackets to allow disconnection of reusable expensive electrode 700 components prior to disposal. For example, disposable substrate 720 may include a bracket 730 and connector 732 for an adhesive gel dispenser 734 (shown in phantom lines), one or more connectors 708 for an external power source or, alternatively a bracket 724 for a rechargeable battery 714 and one or more connectors 702 to controller 330.

Electrode 700, being disposable may employ electromechanical energy converting elements 722 instead of a vibrating motor as described hereinabove. Alternatively, substrate 720 may also include one or more brackets 736 for one or more reusable vibrating cylinder or miniature "pancake" motors 738.

Additionally, or alternatively, disposable substrate 720 may also include some of the aforementioned components such as a controller or printed circuit board (PCB) 716.

FIG. 7C, which is an elevated oblique partially exploded view simplified illustration of the embodiment of FIG. 7A. As shown in FIG. 7C, disposable substrate 720 portion 724-1 is already attached to bridge 726 via port 740-1 by insertion of a tab (not shown) similar to tab 742-2 of disposable substrate 720 portion 724-2. Disposable substrate 720 portion 724-2 is detached and may be attached if desired by inserting tab 742-2 into port 740-2. Ports 740-1 and 740-2 as well as tab 742-2 may be any male-female or other connections known in the art.

It will be appreciated by persons skilled in the art that the present apparatus and method are not limited to what has been particularly shown and described hereinabove. Rather, the scope of the invention includes both combinations and sub-combinations of various features described hereinabove as well as modifications and variations thereof which would occur to a person skilled in the art upon reading the foregoing description and which are not in the prior art.

What we claim is:

1. An apparatus for improving electrode-skin contact, said apparatus comprising:
    a segmented electrode comprising a substrate conformable to topography of the surface of the skin of a body part to which said electrode is to be coupled;
    an array of energy applying surfaces mounted on said substrate via at least one electrically activated electro-mechanical energy converting element;
    a source of energy supplying said energy applying surfaces and said energy converting element; and
    a controller communicating with said source of energy, energy applying surfaces, and said energy converting element,
    wherein electrical activation of the electro-mechanical energy converting elements brings about expansion and contraction of the elements resulting in mechanical movement and causes the surface of a segment of skin to glide under the electrode, distribute more uniformly and conform to the topography of the RF energy applying surfaces.

2. The apparatus according to claim 1, wherein the RF energy applying surfaces define recesses therebetween so that expansion and contraction of the electro-mechanical energy converting element also brings about urging of applied adhesive coupling gel along the recesses forcing out air trapped between the energy applying surfaces and surface of skin, filling air gaps, and improving electrode-skin contact and adhesion.

3. The apparatus according to claim 1, wherein said substrate is made of at least one material selected from a group consisting of rigid, semi-rigid, resilient, stretchable, and contractible materials.

4. The apparatus according to claim 1, wherein said substrate includes two or more portions connected to each other by at least one bridge, and wherein said bridge is a docking platform that accommodates at least one reusable electrode component.

5. The apparatus according to claim 4, wherein said portions are disposable and are pre-coated with a coat of an adhesive gel protected by a protective thin-sheet peel-off layer and include at least one energy applying surface.

6. The apparatus according to claim 4, wherein said bridge is made of the same material as said substrate or a different material selected from a group including elastic expandable band, synthetic fabric, electrically and conductive textile.

7. The apparatus according to claim 4, wherein said bridge is operative to be folded or flexed in any direction to enable said electrode to conform to the topography of the surface of the skin of a specific body part.

8. The apparatus according to claim 4, wherein said portions are disposable and include at least one energy applying surface.

9. The apparatus according to claim 4, wherein said bridge includes a plurality of arms connected to an articulated hub that allows back-and-forth radial movement of said portions about said hub.

10. The apparatus according to claim 1, wherein said electrode substrate includes at least two disposable portions including at least one energy applying surface and connected by at least one reusable bridge.

11. The apparatus according to claim 1, further comprising at least one electrode-skin contact monitoring mechanism operative to communicate a state of said contact to said controller, said state indicative of quality of electrode-skin contact.

12. The apparatus according to claim 1, wherein a sensing mechanism senses skin impedance.

13. The apparatus according to claim 1, wherein said substrate is made of at least one electrically activated electro-mechanical energy converting element.

14. The apparatus according to claim 1, further comprising recesses between said energy applying surfaces and an electrically conductive gel dispenser operative to dispense adhesive coupling gel through pores in said substrate into said recesses.

15. The apparatus according to claim 1, wherein said energy converting element is a vibrating element.

16. An apparatus for improving electrode-skin contact, said apparatus comprising:
    a segmented electrode comprising a reusable substrate conformable to topography of the surface of the skin of a body part to which said electrode is to be coupled;
    a disposable array of energy applying surfaces mounted on said substrate via at least one electrically activated electro-mechanical energy converting element;
    a source of energy supplying said energy applying surfaces and said energy converting element; and
    a controller communicating with said source of energy, energy applying surfaces and said energy converting element,
    wherein electrical activation of the electro-mechanical energy converting elements brings about expansion and contraction of the elements resulting in mechanical movement and causes the surface of a segment of skin to glide under the electrode, distribute more uniformly, and conform to the topography of the RF energy applying surfaces.

17. The apparatus according to claim 16, wherein the RF energy applying surfaces define recesses therebetween so that expansion and contraction of the electro-mechanical energy converting element also brings about urging of applied adhesive coupling gel along the recesses forcing out air trapped between the energy applying surfaces and surface of skin, filling air gaps, and improving electrode-skin contact and adhesion.

18. An apparatus for improving electrode-skin contact, said apparatus comprising:
- a disposable segmented electrode having a substrate comprising at least two disposable portions connected by at least one reusable bridge and having at least one energy applying surface attached to at least one of said disposable portions, said at least one energy applying surface mounted on said substrate via at least one electrically activated electro-mechanical energy converting element;
- a source of energy supplying said energy applying surfaces and said energy converting element; and
- a controller communicating with said source of energy, energy applying surfaces and said energy converting element,
- wherein electrical activation of the electro-mechanical energy converting elements brings about expansion and contraction of the elements resulting in mechanical movement and causes the surface of a segment of skin to glide under the electrode, distribute more uniformly and conform to the topography of the RF energy applying surfaces.

19. The apparatus according to claim 18, wherein the RF energy applying surfaces define recesses therebetween so that expansion and contraction of the electro-mechanical energy converting element also brings about urging of applied adhesive coupling gel along the recesses forcing out air trapped between the energy applying surfaces and surface of skin, filling air gaps, and improving electrode-skin contact and adhesion.

20. The apparatus according to claim 18, wherein said bridge is a docking platform that accommodates at least one reusable electrode component.

21. The apparatus according to claim 20, wherein said at least one reusable electrode component include at least one of a controller, a rechargeable source of power, an adhesive coupling gel dispenser and vibrating elements.

* * * * *